(12) United States Patent
Lalonde

(10) Patent No.: US 6,755,823 B2
(45) Date of Patent: Jun. 29, 2004

(54) MEDICAL DEVICE WITH ENHANCED COOLING POWER

(75) Inventor: Jean-Pierre Lalonde, Verdun (CA)

(73) Assignee: CryoCath Technologies Inc., Kirkland (CA)

( * ) Notice: Subject to any disclaimer, the term of this patent is extended or adjusted under 35 U.S.C. 154(b) by 0 days.

(21) Appl. No.: 09/796,104

(22) Filed: Feb. 28, 2001

(65) Prior Publication Data

US 2002/0120258 A1 Aug. 29, 2002

(51) Int. Cl.[7] ............................................. A61B 18/18
(52) U.S. Cl. ........................ 606/23; 604/509; 606/21; 606/22
(58) Field of Search ........................... 604/509, 21, 22

(56) References Cited

U.S. PATENT DOCUMENTS

| | | | |
|---|---|---|---|
| 5,254,116 A | | 10/1993 | Baust et al. |
| 5,716,353 A | | 2/1998 | Matsuura et al. |
| 5,899,899 A | * | 5/1999 | Arless et al. ................. 606/22 |
| 5,992,158 A | | 11/1999 | Goddard et al. |
| 6,241,718 B1 | * | 6/2001 | Arless et al. ................ 604/509 |
| 6,280,439 B1 | * | 8/2001 | Martin et al. .................. 606/21 |
| 6,319,248 B1 | * | 11/2001 | Nahon .......................... 606/22 |

FOREIGN PATENT DOCUMENTS

| EP | 0 655 225 A1 | 5/1995 |
|---|---|---|
| EP | 0 919 197 A1 | 6/1999 |

* cited by examiner

Primary Examiner—Sabrina Dagostino
(74) Attorney, Agent, or Firm—Christopher & Weisberg, P.A.

(57) ABSTRACT

The present invention provides a medical device to cold treat desired regions. An injection tube with an open distal end, and at least one aperture proximate thereto is disposed inside of a cooling tube, defining a cooling lumen therebetween. A third outer tube member is disposed around the second cooling member, defining a return lumen therebetween. A supply of fluid, regulated by a controller mechanism coupled to the device, flows through the injection lumen, the apertures and the cooling lumen to insulate and cool the fluid supplied into the injection lumen. The supplied fluid flows through the injection lumen and its distal end into the return lumen to cool the surrounding areas external to and proximate the distal end of the device.

16 Claims, 2 Drawing Sheets

MEDICAL DEVICE WITH ENHANCED COOLING POWER

CROSS-REFERENCE TO RELATED APPLICATION

Not applicable.

STATEMENT REGARDING FEDERALLY SPONSORED RESEARCH OR DEVELOPMENT

Not applicable.

1. Field of the Invention

The present invention relates to medical devices, and in particular, to cooling mechanisms for cryogenic devices.

2. Background of the Invention

Catheter-based devices for use in surgical procedures and other medical applications are becoming well known. Recently, the use of low temperature fluids, or cryogens, with such catheters to cold-treat target areas has begun to be explored.

The application of cold to selected body tissues provides a number of advantages over prior catheter devices which alternatively use heat, RF energy, laser light, or other means for treating targeted tissue. A device uses the energy transfer derived from thermodynamic changes occurring in the flow of a cryogen through the device. This energy transfer is then utilized to create a net transfer of heat flow from the target tissue to the device, typically achieved by cooling a portion of the device to very low temperature through conductive and convective heat transfer between the cryogen and target tissue.

Structurally, cooling of the device can be achieved through injection of high pressure cryogen through an orifice into an enclosed expansion chamber. Because the cryogen is supplied at high pressure, ranging up to 800 psia, it is generally a liquid-vapor mixture as it travels through the device to the expansion chamber. Upon injection into the expansion chamber, the cryogen undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature cryogen through the expansion chamber acts to absorb heat from the target tissue and thereby cool the tissue to the desired temperature.

As is well known in the art, of the two processes contributing to the cooling power of the device, evaporative boiling through a change in phase creates a far greater cooling effect through the absorption of latent heat of vaporization, on a specific basis, than merely that of Joule-Thomson cooling alone. Therefore, it is highly desirable to supply the device with a cryogen that is as much in liquid rather than gaseous phase, before the fluid is injected into the expansion chamber to cool tissue. Unfortunately, during transit to the expansion chamber, such as through an elongate catheter, the cryogen supplied typically passes through a region of comparatively high temperature, such as a region of the human body preceding the target area, and is thereby warmed. This warming coupled with head losses in the flow of cryogen down a length of several hundred diameters of tubing, acts to degrade the quality of cryogen from its high pressure liquid form, to a lower pressure, higher temperature, mixed phase form, leading to significantly degraded cooling power of the device. Furthermore, vapor bubbles may form in the injection line, disrupting the smooth flow of cryogen. As is well known to those skilled in the art, the additional adverse effects of sputtering, turbulence, cavitation, and unsteady flow all degrade cooling power.

It is therefore desirable to provide a device which maximizes the cooling power of the flow of cryogenic fluid therethrough, namely through maintaining a steady, uniform supply of high pressure cryogen in liquid phase. It is also desirable to provide a medical device which minimizes cooling losses in the flow of cryogen as it is applied to tissue, as well as maximizing the ratio of the cooling power of the device versus its internal flow lumen diameter.

SUMMARY OF THE INVENTION

The present invention provides a medical device to cold treat desired regions. The device includes an injection tube member defining an injection lumen therein. The injection tube member includes a proximal end, an open distal end, and at least one aperture proximate the distal end. A second cooling member is disposed around the injection tube member, defining a cooling lumen therebetween. A third outer tube member is disposed around the second cooling member, defining a return lumen therebetween. A first fluid pathway is thereby provided for fluid to flow from the injection lumen, through to the aperture in the injection tube, and thereafter through the cooling lumen. A second fluid pathway is provided for fluid to flow from the injection lumen, through the distal end of the injection tube, and thereafter through the return lumen. The device may be coupled to a supply of fluid regulated by a controller mechanism to provide for a pressure gradient throughout the first and second fluid pathways. The flow of fluid through the first fluid pathway insulates and cools the fluid supplied into and flowing through the injection lumen. The flow of fluid through the second pathway cools the surrounding areas external to and proximate the distal end of the device.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

As used herein, the term "cryogen" refers to a fluid substance with properties suitable for: (i) steady flow through ducts of small diameter, (ii) high pressure compression into liquid phase, and (iii) evaporation and expansion to low temperatures. The cryogen may preferably be any suitable, relatively inert "working fluid", such as gases like nitrogen, nitrous oxide, or carbon dioxide, liquids such as chlorodifluoromethane, ethyl alcohol, or Freon (a trademark of DuPont), or any number of other refrigerants or fluids with a high thermal energy transfer capacity and low boiling point, as are commonly known to those skilled in the art.

As used herein, the term "tube" refers to an elongate duct or conduit suitable for conveying a fluid. The tube may comprise of any number of elements or members, and may have a varying range of properties and dimensions, such as length, thickness, and cross-sectional shape.

Figure 1:
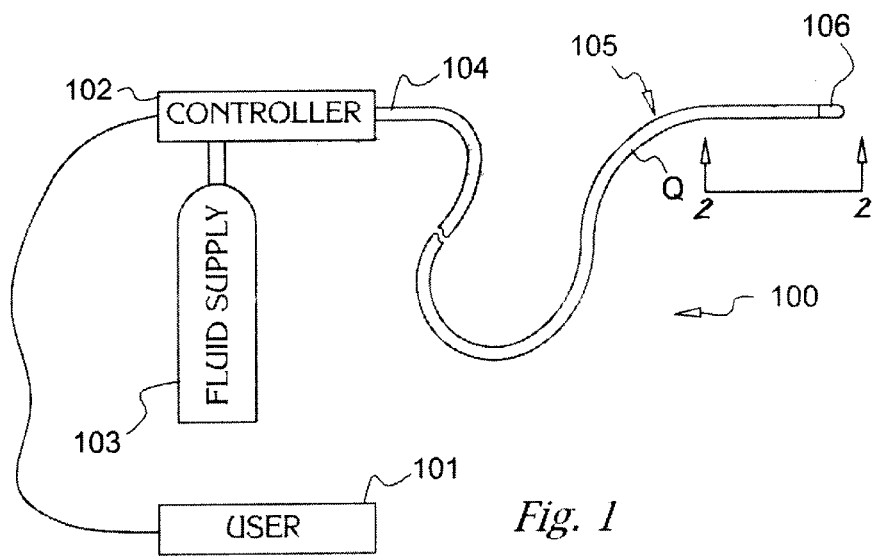
FIG. 1 is a schematic diagram of a medical system that includes enhanced cooling structures in accordance with the invention.

Referring now to the drawings, in which like reference designators refer to like elements, there is shown in FIG. 1 a schematic of a system constructed in accordance with the principles of the present invention, and designated generally as 100. Cryocatheter system 100 preferably includes a controller 102, a cryogen supply 103, and a catheter 104 comprising a distal portion 105, and tip 106. During application, a portion of the catheter 104 is introduced into the body and is placed in contact with or proximate to selected tissue. FIG. 1 illustrates the catheter distal portion 105.

A user 101 interfaces with the controller 102, to control, actuate and operate the components of the system 100. For example, the controller 102 regulates the flow of cryogen into the catheter 104 in response to a command input from user 101 into the controller 102. The controller 102 is preferably any number of suitable mechanical or electronic device components that are capable of receiving and executing programmed instructions, sensor signals, or manual user input as is known in the art.

The cryogen supplied may be either in a liquid or a gaseous state. The cryogen is cooled and/or compressed to a predetermined initial temperature and initial pressure before introduction into the catheter 104. The catheter 104 contains multiple tubes (not shown), preferably made of flexible material such a polymer, fiber, metal, or any combination thereof. The tubes are arranged to create a plurality of lumens (not shown) for the flow of cryogen therethrough. These lumens are arranged to create a closed loop flow path for cryogen such that it circulates through the catheter during operation of the device. This includes an injection lumen (not shown) through which the cryogen is introduced into the catheter 104 to flow from the supply 103 through to the tip 106, and a vacuum return lumen (not shown), through which cryogen eventually flows back from the tip 106. The controller 102 is used to create vacuum pressure conditions (or negative gauge pressure) at the proximate portion of the vacuum return lumen. The initial supply pressure of the cryogen is preferably on the order of 30 to 40 atmospheres, or 400 to 600 psia, much higher than the eventual final pressure in the vacuum return lumen. The resultant negative pressure gradient drives the high pressure cryogen drawn from supply 103 to flow through an injection lumen in catheter 104, to the tip 106, and thereafter to flow back through a vacuum return lumen.

During operation of the device, the catheter 104 is typically introduced into a body, such that the distal portion 105 is disposed in close proximity to a tissue region that is a source of heat Q, thereby warming the cryogen flowing therethrough. In many cryosurgical applications, the length of the distal portion 105 exposed to heat Q may include up to a few hundred diameters of catheter 104. The overall length of catheter 104 from its proximal end to its tip 106 may be several hundred diameters, such that significant head losses are present in the flow of high pressure cryogen therethrough, as is well known to those skilled in the art. Because the cryogen supplied is at as a high pressure and as low a temperature as possible, the dual effect of heat transfer from tissue and head losses through the length of catheter 104 serves to degrade the overall performance of the system 100.

Figure 2:
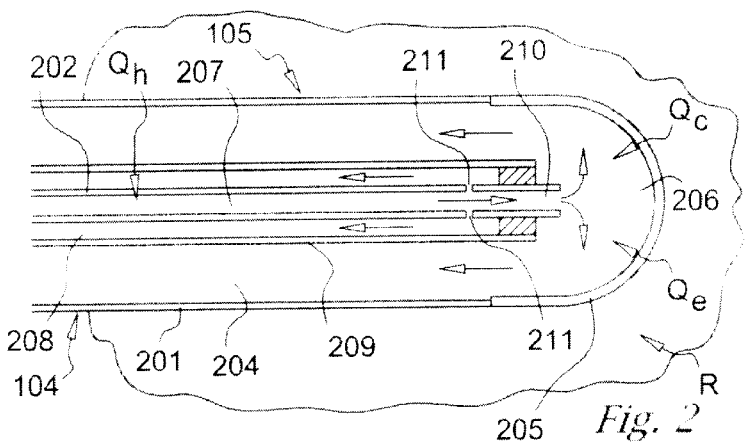
FIG. 2 is a longitudinal cross-sectional view of the distal portion of a catheter, taken along line 2—2, which is part of the system of FIG. 1.

FIG. 2 shows a longitudinal cross-sectional view of the distal portion 105 of the catheter 104, of an exemplary embodiment of the present invention. Referring now to FIG. 2, distal portion 105 comprises an outer tube 201, an injection tube 202, a sub-cooling tube 203, an adhesion element 204, a catheter tip 205, an expansion chamber 206, an injection lumen 207, a sub-cooling lumen 208, a return lumen 209, an injection orifice 210, and at least one sub-cooling aperture 211. Outer tube 201 circumferentially encloses injection tube 202 and sub-cooling tube 203, such that all tubes are preferably coaxially disposed with respect to each other, such that a longitudinal centerline (not shown) of outer tube 201 coincides with the longitudinal centerline of both the injection tube 202 and sub-cooling tube 203. Sub-cooling tube 203 is also disposed coaxially around injection tube 202, such that the longitudinal centerline (not shown) of injection tube 202 coincides with the longitudinal centerline (not shown) of sub-cooling tube 203. It is emphasized that the foregoing spatial arrangement of tubes 201, 202 and 203 are but one particular arrangement, and that any number of alternative arrangements may be used so as to provide for the suitable operational enablement of the present invention.

All of tubes 201, 202, and 203 are preferably made of a flexible solid material, such as polyimide, or other polymer, metal, or combination thereof, suitable for the transport of high pressure fluids, as is well known to those skilled in the art. The distal end of sub-cooling tube 203 is coupled to the distal end portion of injection tube 202, through adhesion provided by adhesion element 204, such that the absolute distal end of sub-cooling tube 203 circumferentially circumscribes the distal end portion of injection tube 202, at a point slightly more proximate than the absolute distal end of injection tube 202. It is understood that any number of adhesion or coupling mechanisms or devices may be used for adhesion element 204, preferably including, but not limited to, a glue, epoxy, or other suitable coupling agent, as is well known to those skilled in the art. Alternatively, injection tube 202 and sub-cooling tube 203 may be formed as a single element, such that the use of adhesion element 204 to couple the distal ends of injection tube 202 and sub-cooling tube 203 is not necessary.

Outer tube 201 is coupled to the catheter tip 205, the catheter tip 205 being disposed at the absolute distal end of the catheter. The tip 205 is preferably made of a thermally-transmissive material, such as a metal or other suitable material of high thermal conductivity. Although many materials and structures may be thermally conductive or thermally transmissive if cooled to a very low temperature, as used herein, a "thermally-transmissive" element is intended to broadly encompass any element that readily conducts heat.

The absolute distal end of injection tube 202 is disposed at a point proximate the tip 205, such that an expansion chamber 206 is defined by the space enclosed by tip 205 inside the distal end of catheter 104, proximate the distal end of injection tube 202. The injection tube 202 further defines an injection lumen 207. High pressure, low temperature cryogen is supplied to the catheter 104, and initially enters the catheter 104 as it flows through the injection lumen 207 towards the expansion chamber 206. At the absolute distal end of the injection lumen 207, the injection tube 202 further comprises an injection orifice 210. Injection orifice 210 is disposed transverse to the flow of cryogen through injection lumen 207. Injection orifice 210 may be an adiabatic nozzle, choked-flow orifice, or other flow regulating structure. Cryogen, upon flowing through the injection lumen 207, exits the injection tube 202 through the injection orifice 210, and flows into the expansion chamber 206. After flowing into the expansion chamber 206, cryogen is induced through a negative pressure gradient to flow back towards the proximate portion of the catheter 104 through the return lumen 209 defined by the interior surface of the outer tube 201 and the exterior surface of the sub-cooling tube 203.

Cryogen flowing through the injection lumen 207 is in mixed liquid and gas phase, at several atmospheres pressure and at a temperature well below standard room temperature. Upon injection into the expansion chamber, the cryogen undergoes two thermodynamic changes. First, the gas phase of the cryogen expands through a positive Joule-Thomson throttling process, which may be substantially isenthalpic, but acts to substantially lower the pressure and the temperature of the cryogen. The resulting low pressure, very low temperature cryogen gas flows through the expansion chamber 206, through to the return lumen 209. This flow of cryogen creates both conductive and convective heat transfer with respect to target region R proximate the catheter tip 205. The cumulative effect of this heat transfer, shown as Qc in FIG. 2, serves to cool any tissue in region R to a desired temperature. Second, upon injection through orifice 210, a portion of the liquid phase of the cryogen evaporatively boils, absorbing latent heat vaporization from the surrounding target region R. This evaporative absorption of heat, labeled in FIG. 2 as Qe, further cools the target tissue. The magnitude of heat transfer rates Qc and Qe may vary widely depending on the particular refrigerant used, although Qc is generally smaller than Qe, such that the overall cooling power of the device is mainly attributable to evaporative cooling rather than conductive or convective heat transfer.

The arrangement of sub-cooling tube 203 coaxially around injection tube 202 defines a sub-cooling lumen 208, circumferentially disposed around the exterior of injection tube 202. At a point proximate the distal end of injection tube 202, injection tube 202 contains at least one sub-cooling aperture 211. At least one aperture 211 is preferably of much smaller diameter than orifice 210. As cryogen flows through the injection lumen 207, before exiting the lumen 207 through orifice 210, the cryogen flows past the sub-cooling apertures 211. The proximate ends of all of tubes 201, 202, 203, and lumens 207, 208, 209 are coupled to the controller 102 shown in FIG. 102, such that the static pressures in all of lumens 207, 208, and 209 may be regulated and controlled during operation of the device. The static pressure in the sub-cooling lumen 208 is maintained at a level above atmospheric pressure, above that of the static pressure in return lumen 209, but still well below the static pressure in the injection lumen 207. Because of this pressure differential, although a majority of the cryogen flows from the injection lumen 207 through orifice 210, a portion of the cryogen flow is directed through the apertures 211 to flow into the sub-cooling lumen 208. This cryogen then flows through the sub-cooling lumen 208 back to the proximate portion of the catheter, whereupon the return lumen and sub-cooling lumen are joined (not shown) and all of the cryogen flowing back towards the controller 102 after cir-culating through the device is collected and either disposed of or recirculated.

The flow of cryogen through the sub-cooling lumen 208 acts to insulate the flow of cryogen in the injection lumen 207 from the heat being transferred therein by the surrounding warm tissue in region R, shown in FIG. 2 as Qh. Although, the warming effects of Qh may be minimized by the use of low thermal-transmissivity materials in outer tube 201, as the cryogen flows in the injection tube throughout the length of the distal portion 105 of the cryocatheter, the effects of Qh may significantly (i) change a portion of the supplied cryogen from liquid to gaseous phase, and (ii) increase head pressure losses and raise the temperature of the cryogen supplied, such that by the time the cryogen is injected into expansion chamber 206, the cooling power of the device is degraded. Thus, arrangement of the sub-cooling tube 203 around injection tube 202 creates a heat exchanger for the cryogen flowing therethough. The heat exchanger acts in two ways, such that the overall effect of the flow of cryogen through the sub-cooling lumen 208 is to "sub-cool" the cryogen flowing in injection lumen 207. First, the flow of cryogen through sub-cooling lumen 208 both insulates the injection lumen 207 from the warming effects of Qh, and provides for thermal energy transport and diffusion of heat away from the injection tube 202. Second, the flow of cryogen through sub-cooling lumen 208 itself provides for additional condensation and cooling of the cryogen in injection lumen 207 through the conductive and convective heat transfer with the flow of low pressure and temperature cryogen in the sub-cooling lumen 208. All of these effects serve to provide a greater proportion of liquid phase cryogen flow through the injection lumen 207 to the orifice 210, prevent unnecessary warming the cryogen, and thus enable greater evaporative cooling and more efficient gas expansion of the cryogen upon injection into the expansion chamber.

Figure 3:
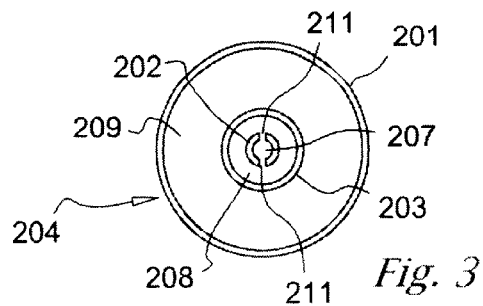
FIG. 3 is a transverse cross-sectional view of the distal portion of the device taken from section 3—3 in FIG. 2.

FIG. 3 shows a transverse cross-sectional view of the catheter 104 taken along section 3—3 in FIG. 2, illustrating the spatial arrangement of outer tube 201, injection tube 202, sub-cooling tube 203, injection lumen 207, sub-cooling lumen 208, and apertures 211. Referring now to FIG. 3, the arrangement of the apertures 211 in injection tube 202 allows for the flow of cryogen from the injection lumen 207, through the apertures 211 and into the sub-cooling lumen 208. Apertures 21 1 may be of any number, and may be disposed along multiple cross-sections of injection tube 202. Preferably, the injection tube inner diameter ranges from 0.004 to 0.06 inches; the sub-cooling tube inner diameter is approximately 0.09 inches; and the outer tube inner diameter is approximately 0.15 inches. As is well known to those skilled in the art, it is understood that the particular dimensions of the device may vary depending on the particular application of the invention and without comprising its fundamental functionality.

Figure 4A:
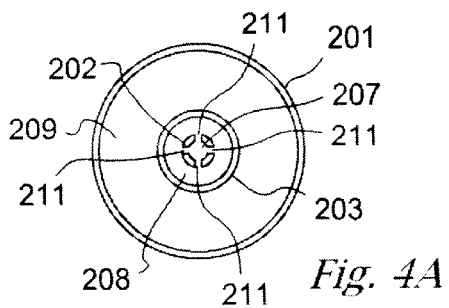
FIG. 4A is an enlarged view of an alternate arrangement of the device as shown in FIG. 3, taken from section 3—3 in FIG. 2.
Figure 4B:
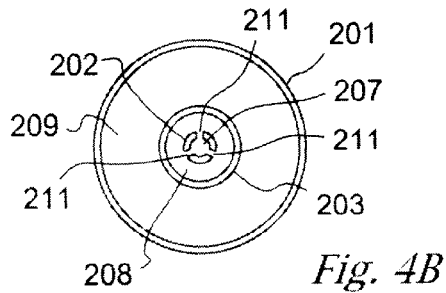
FIG. 4B is an enlarged view of another alternate arrangement of the device as shown in FIG. 3, taken from section 3—3 in FIG. 2.

FIGS. 4A and 4B show additional cross-sectional views of the injection tube 202 and sub-cooling lumen 203 taken from section 3—3 in FIG. 2. Referring now to FIGS. 4A and 4B, the apertures 211 may be arranged radially in any number of patterns, either using a four-aperture configuration as in FIG. 4A, or a three-aperture configuration as in 4B, so as to maximize the sub-cooling efficiency gained through the flow of cryogen from injection lumen 207, through apertures 211, into sub-cooling lumen 208. The cryogen, by entering the sub-cooling lumen 208 through apertures 211 positioned in a variety of locations along the injection tube 202, is uniformly and optimally dispersed through the sub-cooling lumen so as to flow therethrough with a minimum of turbulence, cavitation, unsteady mixing, and friction, all of which induce heat flow into the injection lumen 207, or otherwise degrade the overall cooling efficiency and power of the cryocatheter device.

Figure 5:
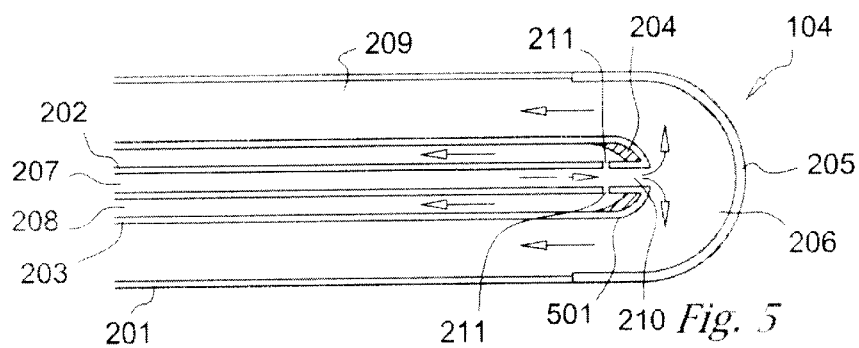
FIG. 5 is a longitudinal cross-sectional view of the distal portion of an alternate arrangement of a catheter which is part of the system shown in FIG. 1.

FIG. 5 shows yet another embodiment of the present invention, further enhancing the overall cooling efficiency of the device. Referring now to FIG. 5, there is shown an additional longitudinal cross-sectional view of the distal portion of catheter 104, comprising an outer tube 201, an injection tube 202, a sub-cooling tube 203, an adhesion element 204, a catheter tip 205, an expansion chamber 206, an injection lumen 207, a sub-cooling lumen 208, a return lumen 209, an injection orifice 210, and at least one sub-cooling aperture 211. The shape of the distal end 501 of the sub-cooling tube 203, as well as the spatial orientation of the coupling of injection tube 202 with sub-cooling 203, may be arranged to provide for enhanced quality flow of cryogen through the expansion chamber 206 upon exiting orifice 210 and flowing through to return lumen 209. In this embodiment, the distal end 501 of sub-cooling tube 203 is curved and coupled to injection tube 202 by means of adhesion element 204. This curvature allows for cryogen exiting the injection tube to flow through the expansion chamber with less turbulence, friction losses, and other unsteady flow effects, than that of the embodiment shown in FIG. 2. This in turn provides for enhanced convective heat transfer between the tip 205 and the cryogen, thereby enhancing the overall cooling power and efficiency of the device. It is understood that the particular coupling arrangement for injection tube 202 and sub-cooling tube 203 is not limited to those embodiments shown in FIGS. 2 and 5, but may be of any number of arrangements suitable for enabling the present invention.

Figure 6:
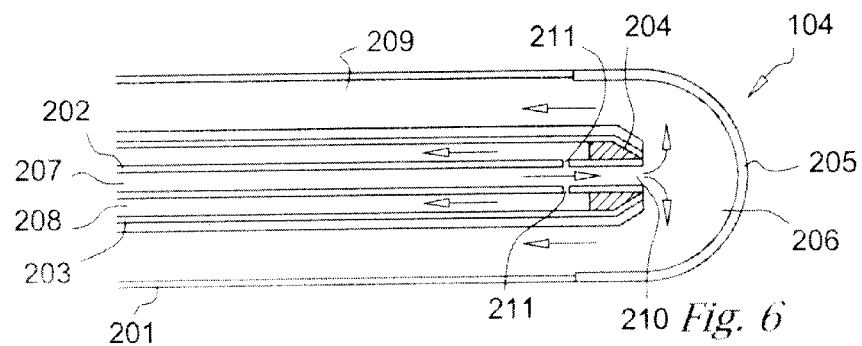
FIG. 6 is a longitudinal cross-sectional view of the distal portion of another alternate arrangement of the catheter.

FIG. 6 shows a longitudinal cross-sectional view of the distal portion of another yet another embodiment of the catheter 104. Referring now to FIG. 6, there is shown an outer tube 201, an injection tube 202, a sub-cooling tube 203, an adhesion element 204, a catheter tip 205, an expansion chamber 206, an injection lumen 207, a sub-cooling lumen 208, a return lumen 209, an injection orifice 210, at least one sub-cooling aperture 211, and an insulation tube 601. The insulation tube 601 covers at least a portion of the outer surface of sub-cooling lumen 203, and is coupled thereto by means of a suitable adhesive or coupling element (not shown). The insulation tube 601 preferably comprises a material of relatively low thermal transmissivity. Heat transfer into the sub-cooling lumen 208, and injection lumen 207 enclosed therein, is significantly reduced by the presence of the insulation tube 601, thereby keeping the cryogen supplied and flowing in injection tube 202 at better conditions for injection into expansion chamber 206. Therefore, the objective of sub-cooling and insulating the cryogen flowing in injection lumen 207 is advanced beyond merely the effects of using a sub-cooling tube 203 alone. It is understood that any number of insulation tubes 601, or other insulation elements such as thin films or coatings may be disposed circumferentially around the injection tube 202 and sub-cooling tube 203, so as to achieve the objectives of the present invention.

Figure 7:
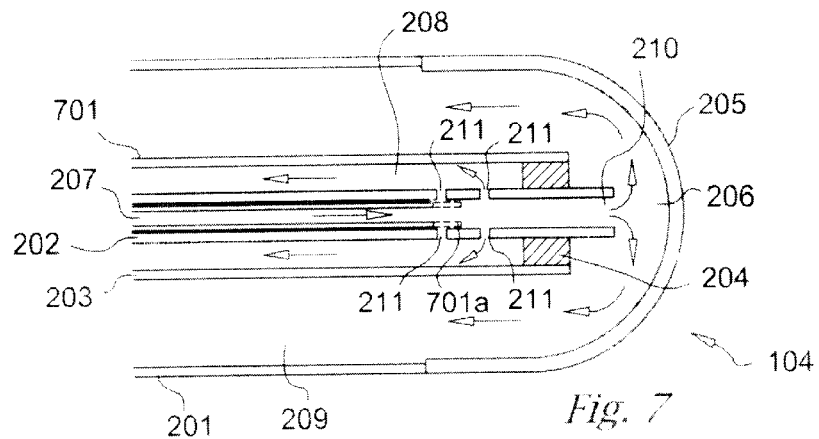
FIG. 7 is an enlarged longitudinal cross-sectional view of the distal portion of yet another arrangement of the catheter.

FIG. 7 shows an enlarged, longitudinal, cross-sectional view of the distal portion of catheter 104, including an outer tube 201, an injection tube 202, a sub-cooling tube 203, an adhesion element 204, a catheter tip 205, an expansion chamber 206, an injection lumen 207, a sub-cooling lumen 208, a return lumen 209, an injection orifice 210, at least one sub-cooling aperture 211, and a blocking tube 701. Blocking tube 701 is slidably disposed in contact with a part of the inner surface of injection tube 202, and extends along a desired length of the injection lumen 207. A suitable control mechanism (not shown) is coupled to blocking tube 701, allowing for the positioning of blocking tube 701 along a plurality of longitudinal positions within the injection lumen 207. In this particular embodiment of the present invention, a set of two apertures 211 are located along two cross-sectional planes of injection tube 202. By sliding the blocking tube from a first position, shown as 701 in FIG. 7, to a second position, shown as 701a in FIG. 7, the number of apertures 211 through which the cryogen may flow from injection lumen 207 through to sub-cooling lumen 208 may be controlled. Thus, the positioning of blocking tube 701 acts to control the flow of cryogen in sub-cooling lumen 208. This in turn allows the user to control the cooling power of the cryocatheter device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising:
   a first member defining an injection lumen therein, the first member having a proximal end, an open distal end, and at least one aperture proximate the distal end,
   a second member disposed around the first member, defining a cooling lumen therebetween, and
   a third member disposed around the second member, defining a return lumen therebetween; the injection lumen, the at least one aperture, and the cooling lumen defining a first fluid path; the injection lumen, the open distal end, and the return lumen defining a second fluid path.

2. The device according to claim 1, further comprising a supply of cryogenic fluid in fluid communication with the injection lumen.

3. The device according to claim 2, further comprising:
   a control mechanism, wherein the control mechanism is coupled to both the supply of cryogenic fluid and each of the first member, the second member, and the third member, the control mechanism regulating the flow of cryogenic fluid through the injection lumen, the cooling lumen, and the return lumen.

4. The device according to claim 3, wherein the control mechanism regulates cryogenic fluid flow to provide a pressure gradient throughout the injection lumen, cooling lumen, and return lumen.

5. The device according to claim 2, wherein the cryogenic fluid is nitrous oxide.

6. The device according to claim 1, wherein the third member further comprises a thermally transmissive distal end portion.

7. The device according to claim 6, wherein the thermally transmissive distal end portion defines an expansion chamber proximate the distal end of the first member, the expansion chamber defining a fluid path for the flow of cryogenic fluid.

8. The cryogenic catheter device according to claim 2, wherein the flow of cryogenic fluid through the first fluid path is substantially less than the flow of cryogenic fluid through the second fluid path.

9. The device according to claim 1, the second member further comprising a distal end portion, the distal end portion of the second member being coupled to the distal end of the first member proximate the at least one aperture of the first member.

10. The device according to claim 1, further comprising a supply of cryogenic fluid in fluid communication with the injection lumen, wherein the at least one aperture is more proximate the supply of cryogenic fluid than the distal end portion of the second elongate member.

11. The device according to claim 9, wherein the distal end portion of the second member is closed.

12. The device according to claim 1, further comprising an insulating member disposed in contact around the second member.

13. The device according to claim 1, further comprising a fourth member disposed within the first member, the fourth member being positionable to block at least one aperture of the first member.

14. A medical device comprising:
- a first member defining an injection lumen therein, the first member having a proximal end, an open distal end, and at least one aperture proximate the distal end,
- a second member disposed around the first member, defining a cooling lumen therebetween, and
- a third member disposed around the second member, the third member having a thermally transmissive distal end portion, the thermally transmissive distal end portion defining an expansion chamber proximate the distal end of the first member, the expansion chamber defining a fluid path for the flow of cryogenic fluid;
- wherein the distal end portion of the second member is closed; and
- wherein the third member defines a return lumen therebetween; the injection lumen, the at least one aperture, and the cooling lumen defining a first fluid path; the injection lumen, the open distal end, and the return lumen defining a second fluid path.

15. A medical device comprising:
- a first member defining an injection lumen therein, the first member having a proximal end, an open distal end, and at least one aperture proximate the distal end,
- a supply of cryogenic fluid in fluid communication with the injection lumen, the cryogenic fluid further comprising nitrous oxide,
- a second member disposed around the first member, defining a cooling lumen therebetween, the second member further comprising a closed distal end portion, the distal end portion being coupled to the distal end of the first member proximate the at least one aperture of the first member, and
- a third member disposed around the second member, the third member defining a return lumen therebetween, the third member further comprising a thermally transmissive distal end portion; the injection lumen, the at least one aperture, and the cooling lumen defining a first fluid path; the injection lumen, the open distal end, and the return lumen defining a second fluid path.

16. The device according to claim 14, further comprising:
- a supply of cryogenic fluid in fluid communication with the injection lumen,
- a control mechanism, wherein the control mechanism is coupled to both the supply of cryogenic fluid and each of the first member, the second member, and the third member, the control mechanism regulating the flow of cryogenic fluid through the injection lumen, the cooling lumen, and the return lumen and to provide a pressure gradient throughout the injection lumen, cooling lumen, and return lumen.

* * * * *